US006441041B1

(12) United States Patent
Clouatre et al.

(10) Patent No.: US 6,441,041 B1
(45) Date of Patent: Aug. 27, 2002

(54) (-)-HYDROXYCITRIC ACID FOR THE PREVENTION OF OSTEOPOROSIS

(76) Inventors: Dallas L. Clouatre, 555 Bryant St. #357, Palo Alto, CA (US) 94301-1704; James M. Dunn, 3236 Hinsdale Pl., Littleton, CO (US) 80112

( * ) Notice: Subject to any disclaimer, the term of this patent is extended or adjusted under 35 U.S.C. 154(b) by 0 days.

(21) Appl. No.: 09/886,499

(22) Filed: Jun. 20, 2001

(51) Int. Cl.$^7$ ............................................. A61K 31/19
(52) U.S. Cl. ...................................................... 514/574
(58) Field of Search ......................................... 514/574

(56) References Cited

U.S. PATENT DOCUMENTS

| | | | |
|---|---|---|---|
| 3,764,692 A | 10/1973 | Lowenstein | 424/279 |
| 3,767,678 A | 10/1973 | Guthrie et al. | 260/343.6 |
| 3,919,254 A | 11/1975 | Guthrie et al. | 260/343.6 |
| 3,993,668 A | 11/1976 | Guthrie et al. | 260/343.6 |
| 4,443,619 A | 4/1984 | Guthrie et al. | 549/518 |
| 5,626,849 A | 5/1997 | Hastings et al. | 424/195.1 |
| 5,656,314 A | 8/1997 | Moffett et al. | 426/271 |
| 5,783,603 A | 7/1998 | Majeed et al. | 514/574 |
| 5,911,992 A | 6/1999 | Braswell et al. | 424/195.1 |
| 5,914,326 A | 6/1999 | McCarty et al. | 514/188 |
| 6,207,714 B1 | 3/2001 | Clouatre et al. | 514/574 |
| 6,217,898 B1 | 4/2001 | Cavazza | 424/450 |
| 6,221,901 B1 | 4/2001 | Shrivastava et al. | 514/458 |
| 2001/0051134 A1 * | 12/2001 | Pandya | 424/44 |

OTHER PUBLICATIONS

Black DM, Cummings SR, Karpf DB, et al. Randomised trial of effect of alendronate on risk of fracture in women with existing vertebral fractures. Fracture Intervention Trial Research Group. Lancet. 1996;348:1535–1541.

Cagnacci A, Soldani R, Yen SS. Melatonin enhances cortisol levels in aged women: reversible by estrogens. J Pineal Res 1997 Mar.;22(2):81–5.

Cagnacci A, Soldani R, Yen SS. Melatonin enhances cortisol levels in aged but not young women. Eur J Endocrinol 1995 Dec.;133(6):691–5.

Cappell MS, Schein JR. Diagnosis and treatment of nonsteroidal anti–inflammatory drug–associated upper gastrointestinal toxicity. Gastroenterol Clin North Am 2000 Mar.;29(1):97–124, vi.

Chesnut CH 3rd, Silverman S, Andriano K, et al. A randomized trial of nasal spray salmon calcitonin in postmenopausal women with established osteoporosis: the prevent recurrence of osteoporotic fructures study. Proof Study Group. Am J Med. 2000;109:267–276.

Clouatre D, Rosenbaum M. The Diet and Health Benefits of HCA, Keats Publishing 1994.

Ettinger B, Black DM, Mitlak BH, et al. Reduction of vertebral fracture risk in postmenopausal women with osteoporosis treated with raloxifene: results from a 3–year randomized clinical trial. Multiple Outcomes of Raloxifene Evaluation (MORE) Investigators, JAMA. 1999;282:637–645.

Ferrari E, Arcaini A, Gornati R, Pelanconi L, Cravello L, Fioravanti M, Solerte SB, Magri F. Pineal and pituitary–adrenocortical function in physiological aging and in senile dementia. Exp Gerontol 2000 Dec.;35(9–10):1239–50.

Goodman RL. The effect of risedronate on the risk of hip fracture in elderly women. N Engl J Med 2001 May 31;344(22):1720–1.

Greenwood MR, Cleary MP, Gruen R, Blase D, Stern JS, Triscari J, Sullivan AC. Effect of (–) –hydroxycitrate on development of obesity in the Zucker obese rat. Am J Physiol. 1981 Jan.;240(1):E72–8.

Harris ST, Watts NB, Genant HK, et al. Effects of risedronate treatment on vertebral and nonvertebral fractures in women with postmenopausal osteoporosis: a randomized controlled trial. Vertebral Efficacy With Risedronate Therapy (VERT) Study Group. JAMA. 1999;282:1344–1352.

Hulley S, Grady D, Bush T, et al. Randomized trial of estrogen plus progestin for secondary prevention of coronary heart disease in postmenopausal women. Heart and Estrogen/Progestin Replacement Study (HERS) Research Group. JAMA. 1998;280:605–613.

Ishihara K,. Oyaizu S, Onuki K, Lim K, Fushiki T. Chronic (–)–hydroxycitrate administration spares carbohydrate utilization and promotes lipid oxidation during exercise in mice. J Nutr. 2000 Dec.;130(12):2990–5.

Lukert BP, Raisz LG. Glucocorticoid–induced osteoporosis. Rheum Dis Clin North Am 1994 Aug;20(3):629–50.

(List continued on next page.)

*Primary Examiner*—Frederick Krass
*Assistant Examiner*—Donna Jogoe

(57) ABSTRACT

(–)-Hydroxycitrate (HCA) supplementation constitutes a novel means of reducing the loss in bone mineral content such as that usually found in osteoporosis and the related loss in bone quality (protection against the corticoid-induced loss in non-mineral bone components). Similarly, HCA supplementation constitutes a novel means of reducing stress-induced bone loss and of reducing other forms of bone loss induced by glucocorticoid-related mechanisms. The discovery that HCA has bone loss-moderating effects allows for the creation of novel and more efficacious approaches to preventing osteoporosis and for maintaining normal bone metabolic functioning even in the face of diet and exercise habits which are less than ideal and in the face of chronic stress. Furthermore, this discovery makes possible the development of adjuvant modalities which can be used to improve the results realized through the employment of conventional anti-osteoporosis/bone protective remedies. Controlled release can be used to provide a sustained and modulated amount of the active to the body as desired and therefore to regulate the use of the compound.

6 Claims, No Drawings

OTHER PUBLICATIONS

Lukert BP. Glucocorticoid–induced osteoporosis. South Med J 1992 Aug.;85(8):2S48–51.

McCarty MF. Promotion of hepatic lipid oxidation and gluconeogenesis as a strategy for appetite control. Medical Hypotheses 1994;42:215–225.

McClung MR, Geusens P, Miller PD, Zippel H, Bensen WG, Roux C, Adami S, Fogelman I, Diamond T, Eastell R, Meunier PJ, Reginster JY. Effect of risedronate on the risk of hip fracture in elderly women. Hip Intervention Program Study Group. N Engl J Med. 2001 Feb. 1;344(5):333–40.

Mashiba T, Turner CH, Hirano T, Forwood MR, Johnston CC, Burr DB. Effects of suppressed bone turnover by bisphosphonates on microdamage accumulation and biomechanical properties in clinically relevant skeletal sites in beagles. Bone 2001 May;28(5):524–31.

Sullivan AC, Triscari J. Metabolic regulation as a control for lipid disorders. I. Influence of (–)-hydroxycitrrate on experimentally induced obesity in the rodent. American Journal of Clinical Nutrition 1977;30:767.

Sullivan, Ann C. and Joseph Triscari. Possible interrelationship between metabolite flux and appetite. In D. Novin, W. Wyriwicka and G. Bray, eds., Hunger:Basic Mechanisms and Clinical Implications (New York: Raven Press,1976) 115–125.

Sullivan AC, Gruen RK. Mechanisms of appetite modulation by drugs. Federation Proceedings 1985;44,1:139–144.

Wallace JL, Dicay M, McKnight W, Bastaki S, Blank MA. N–bisphosphonates cause gastric epithelial injury independent of effects on the microcirculation. Aliment Pharmacol Ther. 1999 Dec.;13(12):1675–82.

The Writing Group for the PEPI. Effects of hormone therapy on bone mineral density: results from the postmenopausal estrogen/progestin interventions (PEPI) trial. JAMA. 1996;276:1389–1396.

\* cited by examiner

(-)-HYDROXYCITRIC ACID FOR THE PREVENTION OF OSTEOPOROSIS

BACKGROUND OF THE INVENTION

1. Field of the Invention

This invention relates to pharmaceutical compositions containing (-)-hydroxycitric acid useful for preventing osteoporosis and other forms of bone loss.

2. Description of Prior Art

Osteoporosis is Latin for "porous bones." It is a progressive condition in which the bones gradually lose their strength and density. As a living tissue, the bone is continuously "remodeled" as it renews itself, responds to damage, and so forth. It constantly is both releasing and absorbing new calcium. As is true of all other tissues, the bone renews itself with a turnover of its cells over time. Bone loss results when the balance of the constructive and destructive processes is tipped from equilibrium towards a loss of calcium and other bone components. An estimated 1.3 million older Americans suffer broken bones every year because of osteoporosis. Wrists, hips, and spinal vertebrae are the most susceptible areas. Women are far more susceptible than are men and suffer about 80% of the injuries caused by this condition. Nevertheless, as this number indicates, a substantial number of men also suffer from osteoporosis. At least in part, this gender-based disproportion in injuries appears to reflect the fact that males begin with larger and denser bones, hence can lose more bone mass and yet still not suffer damage. Still, there is more to it than this. By the age of 65, men on average have lost approximately 9% of their bone mass, whereas women have lost 26% of their bone mass on reaching this age.

Most discussions of osteoporosis focus on the loss of calcium. In fact, this is a major error in analysis. Although the contemporary public health emphasis in maintaining bone health is always upon calcium because calcium is the major component of the bones, even with regard to the inorganic components of bone, calcium may not be the most important in preventing demineralization. The bone consists of both inorganic mineral components and organic components. Osteomalacia is the technical name for the softening of the bones which results from a lack of calcium in the diet. In osteoporosis, not only calcium and other minerals, but also the non-mineral bone matrix, which consists of collagen and proteins, is disrupted. The consensus is that in postmenopausal women the fall in estrogen levels is a major factor in declining bone mineral density, yet there are good reasons for doubting that this is the whole of the answer. Indeed, estrogen is not even approved for the treatment of osteoporosis because recent clinical studies, namely the Heart and Estrogen/Progestin Replacement Study (HERS) and the Postmenopausal Estrogen/Progestin Interventions (PEPI) did not show any fracture reduction in the treatment groups even though a reduction in the loss in bone mineral density (BMD) was reported. (Hulley S, et al. Randomized trial of estrogen plus progestin for secondary prevention of coronary heart disease in postmenopausal women. Heart and Estrogen/Progestin Replacement Study (HERS) Research Group. JAMA. 1998;280:605–613; The Writing Group for the PEPI. Effects of hormone therapy on bone mineral density: results from the postmenopausal estrogen/progestin interventions (PEPI) trial. JAMA. 1996;276:1389–1396.)

More successful in preventing bone loss, at least in the short term, than hormone replacement therapy (HRT) is treatment with bisphosponates. Randomized clinical trials have demonstrated that vertebral fractures in postmenopausal women are reduced by treatment with the bisphosphonates alendronate, risedronate or raloxifene, and also with nasal calcitonin. The bisphosphonates also reduce the incidence of hip fractures in postmenopausal women and have an additive benefit in subjects receiving calcium and vitamin D supplements. (Black DM, et al. Randomised trial of effect of alendronate on risk of fracture in women with existing vertebral fractures. Fracture Intervention Trial Research Group. Lancet. 1996;348:1535–1541; Ettinger B, et al. Reduction of vertebral fracture risk in postmenopausal women with osteoporosis treated with raloxifene: results from a 3-year randomized clinical trial. Multiple Outcomes of Raloxifene Evaluation (MORE) Investigators. JAMA. 1999;282:637–645; Harris S T, et al. Effects of risedronate treatment on vertebral and nonvertebral fractures in women with postmenopausal osteoporosis: a randomized controlled trial. Vertebral Efficacy With Risedronate Therapy (VERT) Study Group. JAMA. 1999;282:1344–1352; Chesnut CH 3rd, et al. A randomized trial of nasal spray salmon calcitonin in postmenopausal women with established osteoporosis: the prevent recurrence of osteoporotic fractures study. PROOF Study Group. Am J Med. 2000;109:267–276).

All of the antiresorptive agents currently approved for the treatment of osteoporosis—alendronate, risedronate, raloxifene, and nasal calcitonin—therefore can be said to decrease bone resorption. However, not one of these compounds induces new bone formation. In fact, antiresorptive agents appear to prevent new bone formation; there are grounds to fear that after a period of 3 to 4 years, they actually may increase the fracture rate. (Goodman R L. The effect of risedronate on the risk of hip fracture in elderly women. N Engl J Med 2001 May 31;344(22):1720–1; Mashiba T, et al. Effects of suppressed bone turnover by bisphosphonates on microdamage accumulation and biomechanical properties in clinically relevant skeletal sites in beagles. Bone 2001 May;28(5):524–3 1).

Consequently, there is a finite limit to the benefits of antiresorptive agents even under the best circumstances. Moreover, the bisphosphonates can cause serious side effects involving the gastrointestinal tract. (Wallace J L, et al. N-bisphosphonates cause gastric epithelial injury independent of effects on the microcirculation. Aliment Pharmacol Ther. 1999 December;13(12):1675–82.) The bisphosphonates alendronate, risedronate and raloxifene may prove particularly unsafe when used in combination with the nonsteroidal anti-inflammatory drugs so commonly taken by the elderly. (Cappell M S, Schein J R. Diagnosis and treatment of nonsteroidal anti-inflammatory drug-associated upper gastrointestinal toxicity. Gastroenterol Clin North Am 2000 March 29(1):97–124, vi).

The notion that it is the age-related decline in estrogen which is primarily responsible for bone loss in aging women remains strongly entrenched in the medical mind. HRT, treatment with bisphosphonates and recommendations for ever higher levels of calcium intake—a dietary recommendation which has produced clinically significant, but nonetheless unimpressive results—constitute almost the whole of the modem medical arsenal against osteoporosis. Many other alternatives have gone largely unexplored. For instance, it is well-established that bone loss is one of the most devastating side effects of glucocorticoid treatment for rheumatic conditions because these compounds inhibit calcium transport, cause secondary hyperparathyroidism, hypogonadism, and impairment of osteoblast function. (Lukert B P, Raisz L G. Glucocorticoid-induced osteoporosis. Rheum Dis Clin North Am 1994 August 20(3):629–50.) The incidence of osteoporosis in patients receiving long-term glucocorticoid therapy is roughly 50%. Trabecul bone is lost more rapidly than is cortical bone with such treatment. Again, it should be that the cause of glucocorticoid-induced bone loss is multifactorial. The gastrointestinal absorption of calcium falls even as urinary excretion rises; the production of gonadal hormones decreases; and bone formation is inhibited in the presence of glucocorticoids, whereas resorption is enhanced. (Lukert B P. Glucocorticoid-induced osteoporosis. South Med J 1992 August 85(8):2S48–51.)

Endogenous glucocorticoid levels typically increase as humans age and remain chronically elevated and/or dysregulated in comparison with the levels found in young adults. According to various studies, a significant increase of serum cortisol levels during evening- and night-times is found in elderly subjects when compared to young controls. Similarly, the circadian amplitude of the cortisol rhythm is significantly reduced in relation to age. More generally, the sensitivity of the hypothalamic-pituitary-adrenal axis to steroid feedback is significantly impaired in elderly subjects. (Ferrari E, et al. Pineal and pituitary-adrenocortical function in physiological aging and in senile dementia. Exp Gerontol 2000 December 35(9–10):1239–50.)

Unfortunately, the options for reducing the elevated and dysregulated glucocorticoid levels characteristic of advancing age and, likewise, prolonged stress, are limited. One powerful antagonist to glucocorticoids is mifepristone, the drug RU 486 now being used as the "morning after" pill to prevent conception. This compound does not appear to be appropriate for chronic ingestion. Another antagonist to the glucocorticoids—seemingly the "natural" choice—is the pineal hormone melatonin taken orally. Paradoxically, however, in postmenopausal women oral melatonin treatment increases rather then decreases cortisol levels. Hence this "natural" treatment would appear to be of little use in preventing bone loss in just those women who need it most. (Cagnacci A, et al. Melatonin enhances cortisol levels in aged women: reversible by estrogens. J Pineal Res 1997 March 22(2):81–5; Cagnacci A, et al. Melatonin enhances cortisol levels in aged but not young women. Eur J Endocrinol 1995 December 133(6):691–5.)

Unrelated to osteoporosis, to bone loss more generally, and to glucocorticoid regulation according to published literature are the actions of (–)-hydroxycitric acid. Instead, (–)-hydroxycitric acid (abbreviated herein as HCA), a naturally-ocurring substance found chiefly in fruits of the species of Garcinia, and several synthetic derivatives of citric acid have been investigated extensively in regard to their ability to inhibit the production of fatty acids from carbohydrates, to suppress appetite, and to inhibit weight gain. (Sullivan A C, Triscari J. Metabolic regulation as a control for lipid disorders. I. Influence of (–)-hydroxycitrrate on experimentally induced obesity in the rodent. American Journal of Clinical Nutrition 1977;30:767.)

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffinann-La Roche, have been summarized in at least two U.S. Patents. In U.S. Pat. No. 5,626,849 these mechanisms are given as follows: "(–) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (–) HCA increase the production and storage of glycogen (which is found in the liver, small intestine and muscles of mammals) while reducing both appetite and weight gain. (–) Hydroxycitric acid also causes calories to be burned in an energy cycle similar to thermogenesis . . . (–) HCA also increases the clearance of LDL cholesterol . . ." U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty MF. Promotion of hepatic lipid oxidation and gluconeogenesis as a strategy for appetite control. Medical Hypotheses 1994;42:215–225) is maintained in U.S. Pat. No. 5,914,326.

Almost all of the primary research performed on HCA was carried out by Hoffmnan-La Roche nearly three decades ago. The conclusion of the Roche researchers was that "no significant differences in plasma levels of glucose, insulin, or free fatty acids were detected in (–)-hydroxycitrate-treated rats relative to controls. These data suggest that peripheral metabolism, defined in the present context as metabolite flux, may be involved in appetite regulation . . ." (Sullivan, Ann C. and Joseph Triscari. Possible interrelationhip between metabolite flux and appetite. In D. Novin, W. Wyriwicka and G. Bray, eds., Hunger: Basic Mechanisms and Clinical Implications (New York: Raven Press,1976) 115–125.) No Roche data was ever published linking HCA to changes in glucocorticoid levels. No conclusions were ever presented which suggested that HCA is useful in preventing bone loss. Some early preliminary work showed that labeled $^{14}C$ attached to HCA found its way into the brain. (Sullivan A C, Triscari J. Metabolic regulation as a control for lipid disorders. I. Influence of (–)-hydroxycitrrate on experimentally induced obesity in the rodent. American Journal of Clinical Nutrition 1977;30:767.) However, work published by the same authors at a later date indicated otherwise. "Hydroxycitrate, chlorocitrate, and epoxyaconitate, compounds that are structurally similar to the tricarboxylic acid cycle intermediate citric acid, but that differ markedly in biochemical activity, have recently been evaluated in animals for effects on appetite. Because neither these compounds nor their metabolites enter the brain, their primary effects on food intake occur by peripheral mechanisms." (Sullivan A C, Gruen R K. Mechanisms of appetite modulation by drugs. Federation Proceedings 1985;44, 1:139–144.)

The present inventors have discovered that HCA not only reduces glucocorticoid levels in animals, but also, and probably as a direct result, increases mineral retention. The projected increase in body mineral content has been found to be true in young rats ingesting a 70% glucose diet and, similarly, in middle-aged rats consuming a diet in which 30% of the energy is derived from fats, i.e., a diet more typical of human beings. Slight, but consistent increases in carcass protein content in these animals suggests, as well, that there is protection against the corticoid-induced loss in non-mineral bone components.

Of the readily available forms of HCA, only the potassium and sodium salts of HCA are absorbed well enough to be effective agents at tolerable levels of ingestion. Reasons for this are given in the inventors'copending U.S. Patent Application "Potassium (–)-Hydroxycitric Acid Methods For Pharmaceutical Preparations For Stable And Controlled Delivery." Derivatives of HCA may also be active and effective in this regard. (U.S. Pat. Nos. 3,993,668; 3,919, 254; 3,767,678.) Liquid forms of HCA currently in use are irritating to the digestive system, depending upon the dose, and may cause an elevation of stress hormones as a result. Researchers have found that animals given high doses of the liquid form of the compound orally exhibit stress behavior. (Ishihara K, et al. Chronic (−)-hydroxycitrate administration spares carbohydrate utilization and promotes lipid oxidation during exercise in mice. J Nutr. 2000 December; 130(12) :2990–5.) Similarly, the ethylenediamine salts of HCA used in some of the later research performed by Hoffman-La Roche are known to be irritating and even toxic, properties which are due to the ethylenediamine ligand and not to the HCA. In contrast to the quite limited efficacy found with the calcium salt and some other delivery forms of HCA, the impact of ingestion of appropriate amounts of the appropriate salts of HCA in reducing glucocorticoid levels has been shown to be powerfully statistically significant.

Therefore, the current invention teaches that HCA supplementation constitutes a novel means of reducing the age-related loss in bone mineral content and the related loss in bone quality (protection against the corticoid-induced loss in non-mineral bone components). Similarly, the invention teaches that HCA supplementation constitutes a novel means of reducing stress-induced bone loss and of reducing other forms of bone loss induced by glucocorticoid-related mechanisms.

SUMMARY OF THE INVENTION

The inventors have discovered that HCA supplementation constitutes a novel means of reducing the loss in bone mineral content usually termed osteoporosis and the related loss in bone quality (protection against the corticoid-induced loss in non-mineral bone components). Similarly, the inventors have discovered that HCA supplementation constitutes a novel means of reducing stress-induced bone loss and of reducing other forms of bone loss induced by glucocorticoid-related mechanisms. These action by HCA have not heretofore been recognized. The benefits of HCA in reducing bone loss are especially pronounced with the use of the preferred salt of the acid, potassium hydroxycitrate, and may be further potentiated by the use of a controlled-release form of the compound. The discovery that HCA has bone loss-moderating effects allows for the creation of novel and more efficacious approaches to preventing osteoporosis and for maintaining normal bone metabolic functioning even in the face of diet and exercise habits which are less than ideal and in the face of chronic stress. Furthermore, this discovery makes possible the development of adjuvant modalities which can be used to improve the results realized through the employment of conventional anti-osteoporosis remedies. HCA delivered in the form of its potassium salt is efficacious at a daily dosage (bid or tid) of between 750 mg and 10 grams, preferably at a dosage of between 3 and 6 grams for most individuals. A daily dosage above 10 grams might prove desirable under some circumstances, such as with grossly obese or resistant individuals, but this level of intake is not deemed necessary under normal conditions.

Objects and Advantages

It is an objective of the present invention to provide a novel means of reducing the age-related loss in bone mineral content usually termed osteoporosis and the related loss in bone quality (protection against the corticoid-induced loss in non-mineral bone components). Similarly, the invention is directed to the employment of HCA supplementation to reduce stress-induced bone loss and to reduce other forms of bone loss induced by glucocorticoid-related mechanisms. The present invention has the advantages of safety and absence of side effects (Clouatre D, Rosenbaum M. The Diet and Health Benefiits, Keats Publishing 1994), claims not true of treatment with the current drugs of choice, the bisphosphonates. The glucocorticoid mechanisms influenced by HCA supplementation are returned to levels and responses more typical of young adults, hence the inherent tolerability of HCA as a preventative treatment for osteoporosis. Knowledge of the present invention has the advantage of allowing the use of forms of (−)-hydroxycitric acid, including especially through controlled release formulations, as adjuvants to current drugs designed to stabilize or improve long term bone mineral balance and bone health.

DESCRIPTION OF THE PREFERRED EMBODIMENTS

The free acid form and various salts of (−)-hydroxycitric acid (calcium, magnesium, potassium, sodium and mixtures of these) have been available commercially for several years. Any of these materials can be used to fulfill the invention revealed here, but with varying degrees of success. For reasons given in our co-pending U.S. Patent Application "Potassium (−)-Hydroxycitric Acid Methods For Pharmaceutical Preparations For Stable And Controlled Delivery," these materials are generally useful in this descending order of efficacy: potassium salt, sodium salt, free acid, magnesium salt, calcium salt. A novel method for improving the efficacy and workability of these forms is provided in that application. Exact dosing will depend upon the form of HCA used, the weight of the individual involved, and the other components of the diet. In part due to the need to control the release of this hypoglycemic agent in diabetics, as outlined in the inventors' recently accepted U.S. Pat. No. 6,207,714 covering the employment of HCA as hypoglycemic agent, a controlled release preparation is to be preferred. Controlled release can also be expected to improve results by aiding in maintaining a sustained exposure to the drug as required for therapy.

The previously patented hydroxycitric acid derivatives (mostly amides and esters of hydroxycititric acid, the patents for which are now expired, to wit, U.S. Pat. Nos. 3,993,668; 3,919,254; and 3,767,678) likely are roughly equivalent to the HCA sodium salt in efficacy and can be applied as taught herein by one skilled in the art. However, for the purposes of reducing stress hormone (glucocorticoid) levels, hydroxycitric acid in its free acid form and in its lactone form may prove to be the least desirable of currently available versions of the compound. The free acid and the lactone forms are irritating to the gastrointestinal tract and thus, in the higher dosages required for therapy, may lead to elevations in stress response. Likewise, hydroxycitric acid in its free acid form and in its lactone form may be less desirable for long term use due to their ability to chelate minerals and thereby perhaps lead to mineral loss.

EXAMPLE 1

EFFECTS UPON GLUCOCORTICOID LEVELS

To test the properties of HCA in various forms under conditions similar to those found in human clinical trials, the inventors arranged for male OM rats aged 10 weeks to be fed a diet in which 30% of the calories were obtained from fat under standard conditions. The rats were intubated twice daily with one of three HCA salts or placebo. The amount of HCA in each arm of 5 animals was the minimum dosage which had been found effective in the form of the pure trisodium salt of HCA in tests by Hoffmann-La Roche in animals ingesting a 70% glucose diet, i.e., 0.33 mmoles/kg body weight HCA given twice per day. The HCA salts used were these: CaKHCA=a mixed calcium and potassium HCA salt commercially marketed as being entirely water soluble; KHCA 1=a relatively clean, but still hardly pure potassium salt of HCA with a good mineral ligand attachment supplying 4467 mg potassium/100 grams of material; KHCA 2=an impure potassium salt of HCA with large amounts of gums attached and poor mineral ligand attachment supplying 2169 mg potassium/100 grams of material. At the end of the 60 day experimental period, the animals were sacrificed and data collected as per normal laboratory procedures. The chart below gives the findings with regard to serum insulin, leptin and corticosterone, i.e., the glucocorticoid which in rats performs much the same role as does cortisol in humans.

Both of the potassium (−)-hydroxycitrate arms were superior to the calcium/potassium arm relative to control in reducing insulin, leptin and corticosterone concentrations. Because of the difficulty in achieving significance with only 5 data points per arm, calculations regarding insulin and leptin combined the data from the two KHCA arms. With respect to insulin, the one-tailed P value was a significant 0.0306, and the two-tailed P value fell slightly short of significance at 0.0612. Using this combined data, there was also a significant one-tailed P value difference between the two KHCA arms and the result found with the CaKHCA. With respect to leptin, the two KHCA arms were combined, in part, because of one anomalously high data point and yielded a one-tailed P value which was a significant 0.0241 and a two-tailed P value which was significant at 0.0482. Corticosterone results were highly significant even at 5 data points per arm. KHCA 1 was easily significantly superior to control: the one-tailed P value was a highly significant 0.0048, and the two-tailed P value was a highly significant 0.0096.

| Group | Insulin ng/mL | Leptin ng/mL | Corticosterone ng/mL |
| --- | --- | --- | --- |
| Control | 2.655 | 9.52 | 269.38 |
| Control | 7.077 | 18.94 | 497.87 |
| Control | 4.280 | 34.34 | 265.71 |
| Control | 9.425 | 24.32 | 209.54 |
| Control | 3.798 | 8.40 | 116.12 |
| KHCA 1 | 3.880 | 9.93 | 45.79 |
| KHCA 1 | 4.399 | 7.31 | 33.10 |
| KHCA 1 | 3.181 | 9.25 | 65.57 |
| KHCA 1 | 3.210 | 24.36 | 55.40 |
| KHCA 1 | 3.639 | 9.07 | 84.62 |
| KHCA 2 | 4.427 | 9.13 | 26.02 |
| KHCA 2 | 4.301 | 9.75 | 270.83 |
| KHCA 2 | 3.245 | 8.00 | 45.44 |
| KHCA 2 | 3.695 | 9.16 | 45.63 |
| KHCA 2 | 2.053 | 8.26 | 38.04 |

The findings with regard to serum insulin levels from this trial are at variance with those found in the published literature, but then again almost all such data in past trials has been based upon young animals fed a 70% glucose (as energy) or other similar diet to encourage lipogenesis. A glucose disposal agent which acts at least in part by improving peripheral insulin sensitivity and peripheral disposal of blood glucose in lean tissues will simply be overwhelmed by such a diet once available storage had been filled.

Roche and other past HCA researchers never examined leptin nor corticosterone levels. The novel findings shown here with regard to the reduction in glucocorticoid levels are quite striking and led the inventors to question if there might be physiological effects from HCA supplementation which had been overlooked in the past.

EXAMPLE 2

EFFECTS UPON BODY PROTEIN AND MINERAL CONTENT USING MIDDLE-AGED RATS AND A MODERATELY HIGH FAT DIET

Using the animal experiment described in Example 1, the inventors examined areas which might reasonably be expected to reflect the lowered serum corticosterone levels discovered in this trial. The two most accessible findings concerned body protein and mineral content. However, it quickly became apparent that HCA exhibits powerfully dose-dependent responses which depend both upon the total mount of the compound ingested and the form in which it is supplied. It turned out to be the case that inappropriately low doses have an effect which is the reverse of that expected and that found with adequate dosages.

The biphasic dose response issue on a diet supplying a nontrivial percentage of its calories as fat apparently has not been properly explored before. In this example, the salts supplied to all three active arms contained the same amounts of HCA. Strikingly, the apparently lower availability of HCA for physiologic uptake or usage when delivered in the form of CaKHCA emerged despite the widespread assertion among commercial suppliers of HCA products that issues of bioavailability are adequately addressed simply by making the calcium salt of the compound soluble. Such is not the case. Similarly, the lower quality potassium salt, KHCA 2, in which inadequate amounts of potassium were available to fully occupy all bonding sites, proved to be no better, but also no worse, than placebo as a weight loss agent. Only the relatively clean and relatively fully reacted KHCA 1 showed any positive effect upon food consumption and weight gain in this model. (This data can be found fully in our co-pending U.S. Patent Application, "Correcting Polymorphic Metabolic Dysfunction with (−)-Hydroxycitric Acid.")

As can be seen in the following chart, at the level of intake used experimentally on a 30% fat diet, potassium HCA salts increased both protein and minerals (ash) as percentages of body weight while reducing fat as a percentage of body weight. The CaKHCA salt, in contrast, increased fat and reduced both protein and ash as percentages of body weight. The relatively higher rates of body hydration found in the potassium salt-fed arms primarily represent elevated glycogen stores in muscle, an expected finding supported by Example 3 below.

| Mean | Control wet/dry % | CaKHCA wet/dry % | KHCA 1 wet/dry % | KHCA 2 wet/dry % |
| --- | --- | --- | --- | --- |
| % Body $H_2O$ | 56.70 | 56.06 | 59.96 | 58.93 |
| % Protein | 18.66/43.33 | 17.77/40.68 | 18.95/47.34 | 20.07/48.98 |
| % Fat | 20.42/46.91 | 22.56/51.04 | 17.83/44.51 | 18.27/44.37 |
| % Ash | 2.98/6.87 | 2.37/5.42 | 3.04/7.65 | 2.61/6.37 |

Because body water content distorts the true impact of the various HCA salts upon protein, fat and ash in comparison with control, calculations are also given in terms of dry weight percentages. It should be noted that both KHCA arms increased protein in comparison with control quite markedly. With regard to mineral content, findings were mixed. The non-fully reacted KHCA 2 arm was not superior to control with regard to mineral content. However, the fully reacted KHCA 1 arm caused a fairly striking increase in mineral content. Our interpretation of these results is that (1) non-fully reacted HCA can attach to minerals as a chelator and perhaps lead to reduced uptake in the gut; and (2) when used properly, HCA reduced the bone and lean tissue loss found in control due to the stress of being intubated twice daily and being subjected to normal laboratory animal arrangements. This explanation is consistent with Example 3, which was performed by other researchers. In the case of the CaKHCA arm, poor availability led to reverse effects which are yet to be fully explained. Nevertheless, the clear and novel implication of this example is that HCA might be employed to reduce mineral and tissue loss. The most likely explanation in the light of Example 1 is an effect upon glucocorticoid metabolism.

EXAMPLE 3

EFFECTS UPON BODY PROTEIN AND MINERAL CONTENT USING YOUNG RATS AND A HIGH SUGAR DIET

No prior literature suggests that HCA might be useful in preventing mineral loss, such as that found in osteoporosis and in individuals exposed to chronic stress. However, results similar to those found in Example 2 have been published before, albeit the researchers in question merely treated the increase in protein and ash as percentages of body composition as curiosities. In this experiment, female Zucker lean (Fa/−) and obese (Fa/fa) rats 10 weeks old, 7–8 per arm, were fed HCA as the trisodium (−)-hydroxycitrate salt as a dietary component (52.6 mmol/kg diet) which otherwise consisted of 70% glucose and 1% corn oil for six weeks. (Greenwood M. R, et al. Effect of (−)-hydroxycitrate on development of obesity in the Zucker obese rat. Am J Physiol. 1981 January; 240(1):E72–8.) The results are found below; no dry weight data are available.

| Mean | Control Lean wet/dry % Obese wet/dry % | Tri-NaHCA Lean wet/dry % Obese wet/dry % | Pair-Fed Lean wet/dry % Obese wet/dry % |
|---|---|---|---|
| % Body H$_2$O | 60.0 | 64.3 | 58.3 |
| | 23.5 | 25.8 | 25.7 |
| % Protein | 21.0/NA | 22.0/NA | 20.5/NA |
| | 10.7/NA | 11.8/NA | 10.9/NA |
| % Fat | 14.4/NA | 8.05/NA | 16.6/NA |
| | 63.4/NA | 59.8/NA | 60.9/NA |
| % Ash | 4.6/NA | 4.9/NA | 4.6/NA |
| | 2.4/NA | 2.6/NA | 2.6/NA |

These data are quite interesting. There is a clear trade-off between carcass fat content and carcass water content. Just as in Example 2, HCA in these animals, especially in the Zucker lean arm, increased total body water. Our best guess is that the increased water content represents increased glycogen stores. Further support for this hypothesis comes from the fact that the higher carbohydrate diet led to higher values for carcass water, albeit this conclusion is tenuous given the fact that different strains of rats were used in Example 2 and Example 3. In this example, trisodium (−)-hydroxycitrate increased carcass protein and ash/mineral content in the lean and the obese animals in comparison with control. Therefore, this data published some twenty years ago by Roche researchers would seem to support the results which the inventors found more recently with different animals and a different diet.

EXAMPLE 4

Numerous methods can be given as means of delivering HCA as required by the invention. The following preparation will provide a stable and convenient dosage form.

| Ingredient | Weight | Percent | 1 Kg Batch |
|---|---|---|---|
| 1. Aqueous Potassium Hydroxycitrate | 500 gm | 62.5% | 0.63 |
| 2. Calcium Carbonate | 50 gm | 6.25% | 0.06 |
| 3. Potassium Carbonate | 50 gm | 6.25% | 0.06 |
| 4. Anhydrous Lactose | 150 gm | 18.75% | 0.19 |
| 5. Cellulose Acetate Pthalate Acetate | 50 gm | 6.25% | 0.06 |
| Total | 800 gm | 100.00% | 100.00 |

A. Blend items 1–5 in mixing bowl until smooth and even.

B. Take the liquid and spray into spray-drying oven at 300° C. until white powder forms. When powder has formed, blend with suitable bulking agent, if necessary, and compress into 800 mg tablets with hardness of 10–15 kg. This will mean that each tablet, if starting with 62% KHCA polymer powder, will have about 31% KHCA. However, if the tablets are pressed to 1600 mg, the dose will be equal to 800×62% KHCA.

C. After pressing the granulate through the screen, make sure that it flows well and compress into oblong tablets.

D. Tablets should have a weight of 1600 mg and a hardness of 14 ±3 kg fracture force. When tablets are completed, check for disintegration in pH 6.8, 0.05M KH2PO4. Disintegration should occur slowly over 4–5 hours.

CONCLUSIONS (−)-Hydroxycitrate has a multitude of metabolic functions. The literature teaches that the compound reduces blood lipids, induces weight loss and decreases appetite in both animals and humans. However, the inventors have discovered that HCA supplementation constitutes a novel means of reducing the loss in bone mineral content such as that usually found in osteoporosis and the related loss in bone quality (protection against the corticoid-induced loss in non-mineral bone components). Similarly, the inventors have discovered that HCA supplementation constitutes a novel means of reducing stress-induced bone loss and of reducing other forms of bone loss induced by glucocorticoid-related mechanisms. These action by HCA have not heretofore been recognized. The discovery that HCA has bone loss-moderating effects allows for the creation of novel and more efficacious approaches to preventing osteoporosis and for maintaining normal bone metabolic functioning even in the face of diet and exercise habits which are less than ideal and in the face of chronic stress. Furthermore, this discovery makes possible the development of adjuvant modalities which can be used to improve the results realized through the employment of conventional anti-osteoporosis/bone protective remedies.

We claim:

1. A method for preventing, treating or ameliorating osteoporosis or other forms of bone mineral loss in individuals in need thereof which is comprised of administering orally an effective amount of (−)-hydroxycitric acid.

2. The method of claim 1 where the (−)-hydroxycitric acid is supplied as a therapeutically effective amount of the free acid or its lactone.

3. The method of claim 1 where the (−)-hydroxycitric acid is supplied as a therapeutically effective amount of the alkali metal salts potassium or sodium (−)-hydroxycitrate.

4. The method of claim 1 where the (−)-hydroxycitric acid is supplied as a therapeutically effective amount of the alkaline earth metal salts calcium or magnesium (−)-hydroxycitrate.

5. The method of claim 1 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

6. The method of claim 1 where the (−)-hydroxycitric acid is supplied as a therapeutically effective amount as the free acid, its lactone or as one or more of the salts or other derivatives of the free acid and is delivered in a controlled release form.

* * * * *